United States Patent
Nuesser et al.

(10) Patent No.: US 7,374,574 B2
(45) Date of Patent: May 20, 2008

(54) DEVICE FOR AXIALLY CONVEYING BODY FLUIDS

(75) Inventors: Peter Nuesser, Berlin (DE); Johannes Mueller, Berlin (DE); Hans-Erhard Peters, Berlin (DE); Joerg Mueller, Berlin (DE); Ali Kilic, Berlin (DE); Kurt Graichen, Berlin (DE); Dietmar Ries, Berlin (DE); Klaus Wunderlich, Berlin (DE)

(73) Assignee: Berlin Heart GmbH, Berlin (DE)

( * ) Notice: Subject to any disclaimer, the term of this patent is extended or adjusted under 35 U.S.C. 154(b) by 286 days.

(21) Appl. No.: 10/467,974

(22) PCT Filed: Feb. 18, 2002

(86) PCT No.: PCT/EP02/01739

§ 371 (c)(1),
(2), (4) Date: Jan. 26, 2004

(87) PCT Pub. No.: WO02/066838

PCT Pub. Date: Aug. 29, 2002

(65) Prior Publication Data

US 2004/0116776 A1   Jun. 17, 2004

(30) Foreign Application Priority Data

Feb. 16, 2001   (DE) ............................... 101 08 815

(51) Int. Cl.
*A61M 1/12*   (2006.01)

(52) U.S. Cl. .................... 623/3.13; 600/16; 600/17; 623/3.1; 623/3.15

(58) Field of Classification Search .................. 600/16, 600/17; 623/3.1, 3.13–3.15
See application file for complete search history.

(56) References Cited

U.S. PATENT DOCUMENTS

| | | | |
|---|---|---|---|
| 4,820,301 A | | 4/1989 | Chareire et al. |
| 4,994,078 A | * | 2/1991 | Jarvik ........................ 623/3.14 |
| 5,941,813 A | * | 8/1999 | Sievers et al. ................. 600/16 |
| 6,053,705 A | | 4/2000 | Schöb et al. |
| 6,179,773 B1 | | 1/2001 | Prem et al. |
| 6,186,665 B1 | * | 2/2001 | Maher et al. ................ 384/206 |
| 6,293,901 B1 | | 9/2001 | Prem |
| 6,375,607 B1 | | 4/2002 | Prem |
| 6,742,999 B1 | * | 6/2004 | Nusser et al. ............. 417/423.1 |

FOREIGN PATENT DOCUMENTS

| | | |
|---|---|---|
| WO | WO 94/09274 | 4/1994 |
| WO | WO 98/11650 | 3/1998 |
| WO | WO 00/64030 | 10/2000 |

\* cited by examiner

*Primary Examiner*—Carl Layno
*Assistant Examiner*—Yun Haeng Lee
(74) *Attorney, Agent, or Firm*—Brinks Hofer Gilson & Lione

(57) ABSTRACT

The invention relates to a device for axially conveying body fluids. The aim of the invention is to embody the inflow and outflow area of an axial pump in such a way that the flow is not separated even when it is diverted, thereby maintaining a substantially non-disrupted flow profile.

13 Claims, 3 Drawing Sheets

DEVICE FOR AXIALLY CONVEYING BODY FLUIDS

BACKGROUND

The invention relates to a device for axially conveying body fluids.

In particular, body fluids such as blood which can undergo irreversible changes caused by an energy input, such as in the case of emulsions and dispersions, can run into instable ranges in a disadvantageous manner when being conveyed in corresponding devices such as pumps.

Blood is a particularly sensitive fluid system. This opaque red body fluid of the vertebrates circulates in a self-enclosed vessel system where rhythmic contractions of the heart press the blood into various areas of the organism. In this case, the blood transports the respiratory gases oxygen and carbon dioxide as well as nutrients, metabolic-products and endogenous active ingredients. The blood vessel system including the heart is hermetically isolated from the environment so that, in a healthy organism, the blood does not undergo any changes when it is pumped through the body by way of the heart.

It is known that, when blood comes into contact with non-endogenous materials or as a result of the effect of energy from an external source, it has a tendency to hemolysis and clot formation. Clot formation can be fatal for the organism because it can lead to blockage in the extensive branching profile of the vessel system. Hemolysis describes the condition where the red blood cells are destroyed within the body beyond the physiological dimension.

The causes for hemolysis can be of a mechanical or metabolic nature. Increased hemolysis causes multiple organ damage and can lead to a person's death.

On the other hand it is evident that it is possible in principle, under certain prerequisites with reference to constructive aspects, to support the pumping capacity of the heart or even to replace the natural heart with a synthetic one. However, a continuous operation of implanted heart supporting systems or synthetic hearts is presently only possible with certain limitations heart supporting systems or synthetic hearts is presently only possible with certain limitations because the interactive effects of these artificial products with the blood and the entire organism still always lead to disadvantageous changes of the blood and the organism.

In the state of the art, axial blood pumps are known which mainly consist of a cylindrical tube in which a conveying part, which is executed as an externally located motor stator, is located. The rotor which is provided with a so-called blading, conveys the fluid in an axial direction after it has been made to rotate by means of the motor stator.

In the WO 00/64030 a device for the protective conveying of single- or multiple-phase fluids is described. Where this device is concerned, and in the direction of flow, an inlet guide facility is arranged upstream of the conveying part (rotor) and, as seen in the direction of flow, an inlet guide facility is arranged upstream of the conveying part (rotor) and, as seen in the direction of flow, an outlet guide facility is arranged downstream of the conveying part. Even though the blood in the flow passage zone of the pump does not undergo essentially any disadvantageous changes, the disadvantage is evident to the extent that, in the inflow zone upstream of the inlet guide facility and in the outflow zone downstream of the outlet guide facility of the pump, disrupted flows can form which can lead to a change of the blood.

In the U.S. Pat. No. 4,994,078 a heart pump is described whose outlet and inlet zones have certain flow cross-sections which are characterised by cross-sectional reductions and expansions, respectively. However, this flow pattern of the blood indicated at that location is only inadequately illustrated so that, in the outflow zone, it is not clearly recognisable how the blood flow is conducted further.

The invention is based on the task assignment of executing the inflow zone and the outflow zone of an axial pump in such a way that no flow separation occurs with an envisaged deflection of the flow in these zones, but instead a non-disrupted flow profile remains upheld to the greatest extent.

SUMMARY OF THE INVENTION

Therefore, this is the device according to the invention for the axial conveying of body fluids, consisting of a tube-shaped hollow body (1) transporting the liquid in an essentially axial manner, and in this hollow body (1) there is arranged in axial alignment a conveying part that can be rotated by a motor stator (3) located outside of the hollow body (1) in a pump casing (8), where the conveying part (2) has a rotor blading (5) and where stationary inlet and outlet guide facilities (6, 7) are arranged in the direction of flow upstream and downstream of the conveying part (2), and inflow and outflow zones (10, 11) which are positioned at the hollow body (1) in a flow-direction-changing mode, where in the inflow zone (10) an intake bend (12) having an intake bend angle (15) is positioned at the tube-shaped hollow body (1) and in the outflow zone (11) an outlet bend (13) having an outlet bend angle (14) is positioned at the hollow body (1), and where the intake bend (12) has a cross-sectional reduction in the direction of the inlet guide facility (6) and the outlet bend (13) in the direction of flow up to an outlet cylinder (19) has a cross-sectional reduction, wherein the intake and outlet bends (12, 13) as well as the inlet and outlet channels (17, 18) advantageously consist of flexible material.

A flow diffuser (25) and an outlet channel (17) are arranged in the direction of flow downstream of the outlet cylinder (19).

I a further embodiment of the invention, the flexible material essentially consists of silicone and/or reinforced silicone (fabric). The flexibility of the material allows an optimal operative insertion of the device according to the invention as well as its function in the thoracic area.

In a further embodiment of the invention, the outlet bend and the intake bend only have some individual areas made of flexible material.

The radius of the intake bend and the diameter of the inlet of the intake bend are in a ratio of 1:2.

The flow diffuser has a cross-sectional expansion in the direction of flow.

The formation of the inflow zone and the outflow zone, according to the invention, of a category-related axial pump leads to a situation where the flows can be accelerated very gently without causing disrupted flow regimes. In this case, particularly the formation of the intake bend angle according to the invention, between 45° and 50°, in relation to the change of the flow cross-section, has proved to be very advantageous. The size of the outlet bend angle in this case is between 85° and 95°. The flow profile produced here according to the invention can therefore be characterised by the following advantageous properties:

special form-shaping of the intake bend with permanent acceleration of the flow in the inflow to the inlet guide facility;

optimised inflow to the conveying part by means of a corresponding configuration of the inlet guide facility;

optimised energy transfer in the conveying part;

conditioning of the flow and pressure recovery in the outlet guide facility;

special configuration of the outlet bend with permanent acceleration of the flow in the bent zone;

conditioning of the flow in the area of the connecting piece to the outlet channel, this connecting piece being preferentially provided with a gradual cross-sectional expansion in form of a rotation-symmetrical diffuser. The device according to the invention receives a particularly advantageous embodiment by the selection of elastically adequately form-stable materials, for the intake and outlet bends which can, in this way, accommodate physically-related permanent movements in the area of the connection of the device to the heart chamber (ventricle) and/or to the aorta.

BRIEF DESCRIPTION OF THE DRAWINGS

The invention is described in greater detail with the help of a drawing. The drawings show the following.

DESCRIPTION OF PREFERRED EMBODIMENT

Figure 1:
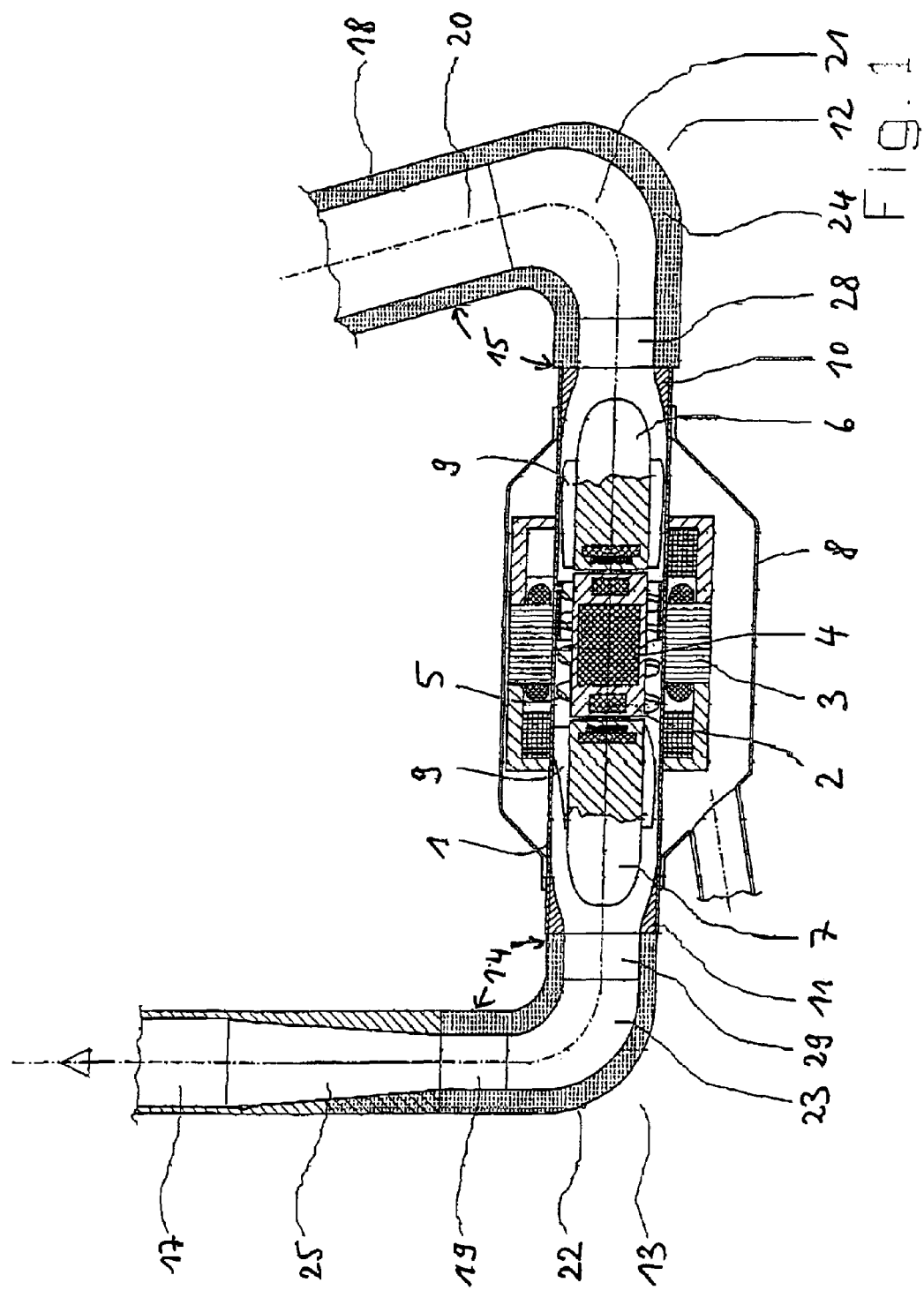
FIG. 1 a schematic cross-sectional illustration of a category-related axial pump with intake and outlet bends.

FIG. 1 shows the schematic illustration of a category-related axial pump with an intake bend 12 and an outlet bend 13. With an intake collar 28, the intake bend 12 is secured to an inflow zone 10 of a cylindrical hollow body 1. With an outlet collar 29, the outlet bend 13 is secured to an outlet flow zone 11 of the cylindrical hollow body 1. As seen in the direction of flow, the cylindrical hollow body contains a stationary inlet guide facility 6 with a guide blading arrangement 9, a floating bearing-located conveying part 2, consisting of a motor rotor 4, a rotor blading arrangement 5 and a back-up ring 30. As seen in the direction of flow, and downstream of the motor rotor 4, a stationary outlet guide facility 7 with an outlet guide blading arrangement 16 is arranged. The motor rotor is caused to rotate by means of a motor stator 3 which is arranged in a pump casing 8. In an axial pump shown here as an example, a flow diffuser 25 is envisaged at the outlet bend 13. By way of an inlet channel 18, the blood to be conveyed enters an inlet cylinder 20 of the intake bend 12 and then, in accordance with the bend routing 24 of the intake bend 12, it is deflected by an intake bend angle 15 in the direction of flow and led into the intake collar 28. The intake bend 12 here and downstream has a permanent cross-sectional narrowing up to the inflow zone 10. The blood is now led via the inlet guide facility 6 and past the motor rotor 4 and by way of the outlet guide facility 7 into the outflow zone 11 of the cylindrical hollow body 1. At this point, the blood enters the outlet collar 29 of the outlet bend 13 and is deflected in the outlet bend 13 in the direction of flow by an outlet bend angle 14. Here again, there is a cross-sectional narrowing of the outlet bend 13. An outlet cylinder 19 of the outlet bend 13 is added here in an exemplary manner at the flow diffuser 25 which has downstream a permanent cross-sectional enlargement in the direction of an outlet channel 17. Based on the arrangement of the intake bend 12 which deflects the blood flow under the intake bend angle 15, and the arrangement of an outlet bend 13 which deflects the blood under the outlet bend angle 14, a non-disrupted flow profile is achieved.

Figure 2:
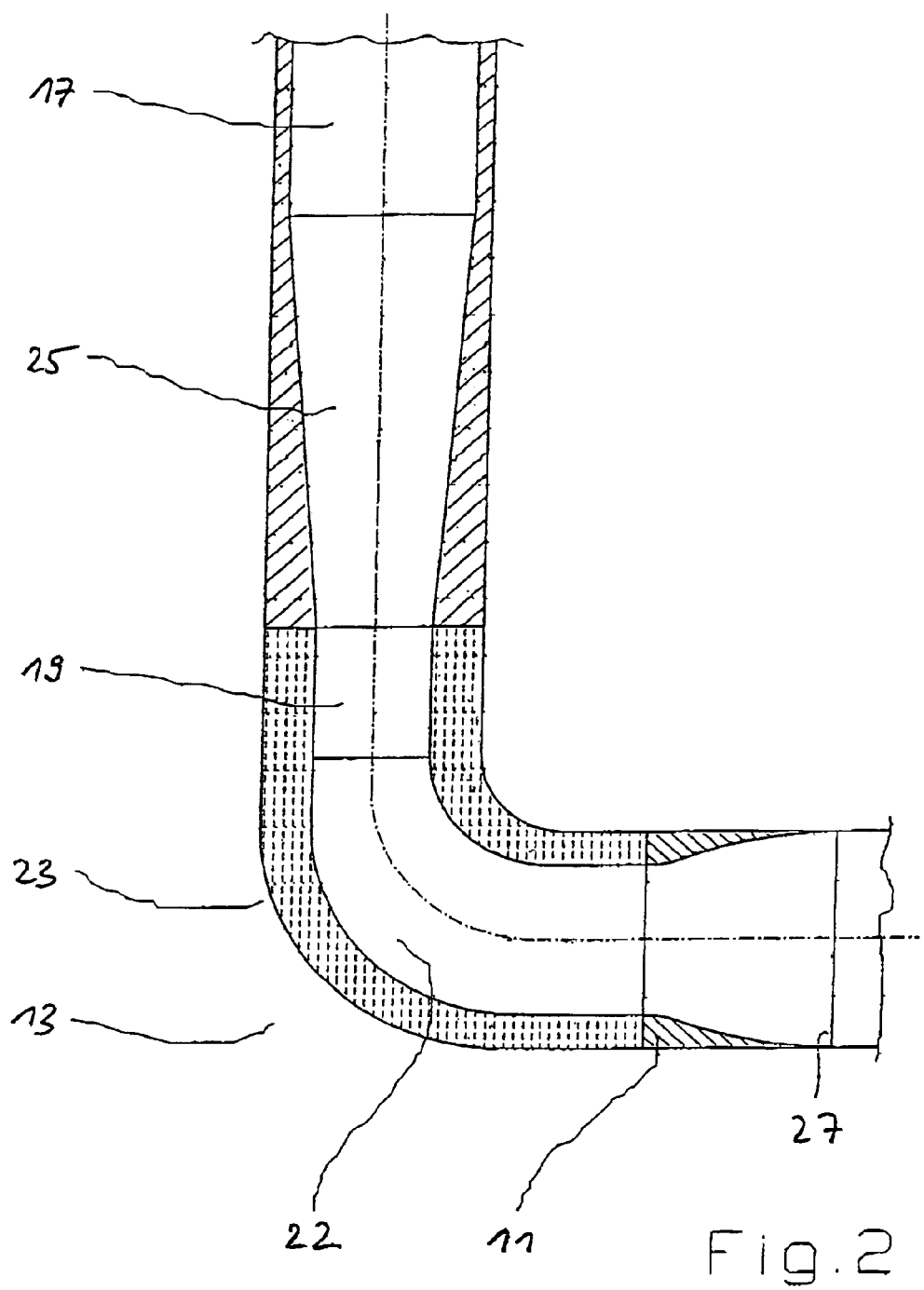
FIG. 2 a schematic cross-sectional illustration of the outlet bend.

FIG. 2 shows in a schematic cross-sectional illustration the outlet bend 13 which leads the blood to be conveyed by way of a pump outlet 27, the outlet flow zone 11 and a bend 23 into the outlet cylinder 19 and then further into the flow diffuser 25 and the outlet channel 17. With this routing method of the flow, a separation of the flowing blood from an inner wall 22 of the outlet bend 13 is advantageously avoided.

Figure 3:
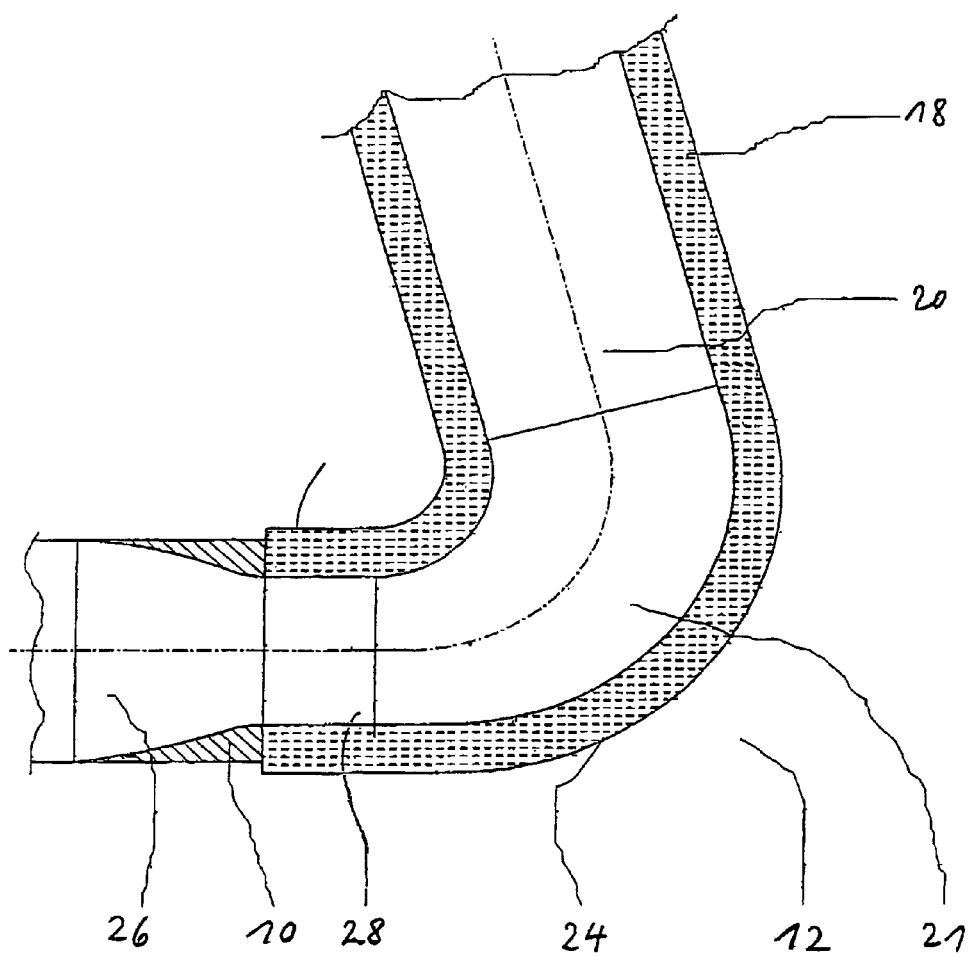
FIG. 3 a schematic cross-sectional illustration of the intake bend

The intake bend 12 as shown in FIG. 3 in a schematic sectional arrangement deflects the blood coming from the inlet channel 18 via the inlet cylinder 20 around an intake bend angle 15 into the inlet collar 28. In this case, a permanent cross-sectional narrowing of the intake bend 12 is effected downstream up to the inlet collar 28. By way of the inflow zone 10, the blood is then conveyed into the pump inlet 26. Due to the permanent flow cross-sectional narrowing existing here according to the invention, no separation of the flow from the wall 21 of the intake bend 12 occurs.

REFERENCED PARTS LIST

1 Hollow body
2 Conveying part
3 Motor stator
4 Motor rotor
5 Rotor blading
6 Inlet guide facility
7 Outlet guide facility
8 Pump casing
9 Guide blading
10 Inflow zone
11 Outflow zone
12 Intake bend
13 Outlet bend
14 Outlet bend angle
15 Intake bend angle
16 Outlet guide blading
17 Outlet channel
18 Inlet channel
19 Outlet cylinder
20 Inlet cylinder
21 Wall
22 Wall
23 Bend
24 Bend
25 Flow diffuser
26 Pump inlet
27 Pump outlet
28 Inlet collar
29 Outlet collar
30 Back-up ring

The invention claimed is:

1. Device for axially conveying body fluids, comprising a tube-shaped hollow body transporting the fluids in an essentially axial manner, and in this hollow body there is arranged in axial alignment a conveying part that can be rotated by a motor stator located outside of the hollow body in a pump casing, where the conveying part has a rotor blading and where stationary inlet and outlet guide facilities are arranged in the direction of flow upstream and downstream of the conveying part, and inflow and outflow zones which are entirely coaxially aligned with the conveying part and positioned at opposite ends of the tube-shaped hollow body surrounding the inlet and outlet guide facilities, an intake bend made entirely of a flexible material leading from an inlet channel and having an intake bend angle, the intake bend being coupled to the inflow zone of the tube-shaped hollow body, the intake bend having a cross-sectional reduction in the direction of the inlet guide facility, and an outlet bend made entirely of a flexible material leading to an outlet channel is arranged having an outlet bend angle, the outlet bend being coupled to the outflow zone of the hollow body, wherein the intake and outlet bends flexible materials accommodate physical movements of the inlet and outlet channels when connected to a heart chamber or aorta.

2. Device according to claim 1, wherein, in the flow direction downstream of the outlet bend, a flow diffuser is arranged.

3. Device according to claim 2, wherein, the flow diffuser has a cross-sectional expansion in the direction of flow.

4. Device according to claim 3, wherein the cross-sectional expansion of the flow diffuser is rotationally symmetric.

5. Device according to claims 1, wherein, the flexible material essentially consists of silicone and/or reinforced silicone.

6. Device according to claim 1, wherein, the outlet bend has a cross-sectional reduction in the direction of flow up to an outlet cylinder.

7. A device according to claim 1 wherein the outlet bend angle is between 85 degrees and 95 degrees.

8. A device for axially conveying body fluids, comprising:
a tube-shaped hollow body for transporting the body fluids through the hollow body in an essentially axial manner,
a conveying part positioned in and arranged in axial alignment with the hollow body, the conveying part having rotor blading defining a flow direction,
a motor stator located outside the hollow body in a pump casing in sufficiently close proximity to cause rotation of the conveying part and rotor blading,
a stationary inlet guide facility arranged upstream of the conveying part towards an inflow zone and a stationary outlet guide facility arranged downstream of the conveying part towards an outflow zone, the inflow zone and the outflow zone being entirely coaxially aligned with the conveying part,
an intake bend entirely made of a flexible material and having an intake bend angle, the intake bend being coupled to the inflow zone adjacent the stationary inlet guide facility and an outlet bend made entirely of a flexible material having an outlet bend angle, the outlet bend being coupled to the outflow zone adjacent the stationary outlet guide facility, the outlet bend including a cross-sectional reduction in the direction of flow to an outlet cylinder remote from the outflow zone, and
an inlet channel arranged at the end of the intake bend remote from the conveying part, and an outlet channel arranged at the end of the outflow bend remote from the conveying part, wherein the intake and outlet bends flexible materials to accommodate physical movements of the inlet and outlet channels when connected to a heart chamber or aorta.

9. The device according to claim 8, wherein a flow diffuser having a cross-sectional expansion in the direction of flow is situated between the outlet cylinder and the outlet channel, the flow diffuser being rotationally symmetric.

10. The device according to claim 8, wherein the flexible materials consist essentially of materials selected from the group consisting of silicone and reinforced silicone.

11. A device according to claim 8 wherein the outlet bend angle is between 85 degrees and 95 degrees.

12. A device for axially conveying body fluids, comprising:
a tube-shaped hollow body for transporting the body fluids through the hollow body in an essentially axial manner,
a conveying part positioned in and arranged in axial alignment with the hollow body, the conveying part having rotor blading defining a flow direction,
a motor stator located outside the hollow body in a pump casing in sufficiently close proximity to cause rotation of the conveying part and rotor blading,
a stationary inlet guide facility arranged upstream of the conveying part towards an inflow zone and a stationary outlet guide facility arranged downstream of the conveying part towards an outflow zone, the inflow zone and the outflow zone being entirely coaxially aligned with the conveying part,
an intake bend made entirely of a flexible material, the intake bend being coupled to the inflow zone adjacent the stationary inlet guide facility and an outlet bend made entirely of the flexible material, the outlet bend being coupled to the outflow zone adjacent the stationary outlet guide facility, the outlet bend including a cross-sectional reduction in the direction of flow to an outlet cylinder, and
an inlet channel arranged at the end of the intake bend remote from the conveying part, and an outlet channel arranged at the end of the outflow bend remote from the conveying part, the inlet and outlet flexible materials selected from the group consisting of silicone and reinforced silicone to accommodate physical movements of the inlet and outlet channels when connected to a heart chamber or aorta.

13. A device according to claim 12 wherein the outlet bend angle is between 85 degrees and 95 degrees.

* * * * *

UNITED STATES PATENT AND TRADEMARK OFFICE
CERTIFICATE OF CORRECTION

PATENT NO.         : 7,374,574 B2                                    Page 1 of 1
APPLICATION NO.  : 10/467974
DATED              : May 20, 2008
INVENTOR(S)        : Peter Nuesser et al.

It is certified that error appears in the above-identified patent and that said Letters Patent is hereby corrected as shown below:

<u>Column 6</u>
Line 5, delete the word "to" after "materials".
Line 45, delete the words "flexible materials" and insert --bends--.

Signed and Sealed this

Fifth Day of August, 2008

JON W. DUDAS
*Director of the United States Patent and Trademark Office*